United States Patent [19]

Kumakura et al.

[11] Patent Number: 4,552,633

[45] Date of Patent: Nov. 12, 1985

[54] FINE PARTICULATE FOR USE IN CLINICAL TESTING AND A PROCESS FOR PRODUCING THEREOF

[75] Inventors: Minoru Kumakura; Isao Kaetsu; Mieko Suzuki; Masakazu Adachi, all of Gunma, Japan

[73] Assignees: Japan Atomic Energy Research Institute, Tokyo; Immunoresearch Laboratories Co., Ltd. Gunma, both of Japan

[21] Appl. No.: 534,661

[22] Filed: Sep. 22, 1983

[30] Foreign Application Priority Data

Sep. 29, 1982 [JP] Japan ................................ 57-170028
Sep. 29, 1982 [JP] Japan ................................ 57-170029
Sep. 29, 1982 [JP] Japan ................................ 57-170030

[51] Int. Cl.$^4$ ........................... C08F 2/48; C08F 2/54; C08F 16/34
[52] U.S. Cl. ................................ 204/159.21; 435/180
[58] Field of Search .................... 204/159.21; 435/180

[56] References Cited

U.S. PATENT DOCUMENTS 4,413,070 11/1983 Rembaum ...................... 204/159.21
4,438,239 3/1984 Rembaum et al. ............. 204/159.21

Primary Examiner—Allan M. Lieberman
Attorney, Agent, or Firm—Browdy and Neimark

[57] ABSTRACT

A fine particulate carrier for use in clinical testing which has a size of 0.5 to 20 microns and a process for producing thereof are herein disclosed.

15 Claims, No Drawings

FINE PARTICULATE FOR USE IN CLINICAL TESTING AND A PROCESS FOR PRODUCING THEREOF

BACKGROUND OF THE INVENTION

1. Technical Field

The present invention relates to micro particles for use in clinical measurements and a process for producing such particles.

2. Description of the Prior Art

In clinical testing by immunochemical techniques, micro particles are used as carriers for determining materials present in trace amounts in boby fluids, such as IgA, IgD, IgE and IgG. Typically, the micro particles used are biological particles such as red corpuscles. These particles are sensitized with an antigen or antibody, which reacts with the antibody or antigen in the sample to cause either hemagglutination or hemagglutination inhibition for determination of the the antibody or antigen present in the sample in a trace amount. Instead of biological carriers, non-biological carriers have recently been used, for example, micro particles of synthetic latices or minerals such as bentonite and rock crystal. For example, in pregnancy diagnosis involving the detection of the human placental gonadotropic hormone in the urine and body fluids of the subject, a latex having anti-HCG adsorbed physically on the surface is mixed with a sample (e.g. serum) to check for the presence of latex aggregation.

Most of the solid micro particles used as carriers in clinical immunochemical assay have no particular bound functional groups on their surface, and the binding of the carrier to an antigen or antibody is simply a physical binding that depends on the adsorption of the antigen or antibody. Therefore, the binding force is weak and frequent dissociation of the antibody-antigen bonding has caused an error in the determination of the target material.

The latices of the conventional non-biological particles most commonly used are in most cases produced by emulsion polymerization using a catalyst in the polymerization system containing low concentrations of a monomer and high concentrations of an emulsifier. The resulting particles have a relatively wide size distribution ranging from 0.01 to 2 microns, with a high incidence of particles smaller than 1 micron. For ordinary immunochemical determination, carrier particles with a size of about 2 to 3 microns are preferred. However, synthesis of micro particles of a 2 or 3 micron size by emulsion polymerization involves several problems such as prolonged reaction time and the need for special process conditions. On the other hand, catalytic polymerization is disadvantageous in that impurities such as catalysts are introduced into the resulting particles to impair their physical properties. But in all likelihood, the swollen latex particles are not necessarily in a spherical form and may have different properties than the latex particles produced by direct polymerization.

SUMMARY OF THE INVENTION

As a result of various studies made to solve the above problems of the conventional art, we have discovered that solid micro particles of a size of 0.5 to 20 microns can be produced from a polymerization system primarily composed of at least one specific monomer by exposing said system to a low dose of light or ionizing radiation at temperatures lower than room temperature.

Therefore, one object of the present invention is to provide a fine particulate carrier for use in clinical testing which has a size of 0.5 to 20 microns.

Another object of the present invention is to provide a process for producing a fine particulate carrier for use in clinical testing having a size of 0.5 to 20 microns and an aldehyde group on the surface by exposing to light or ionizing radiation a polymerizable monomer having an aldehyde group and a polymerizable double bond in the same molecule while maintaining said monomer at temperatures lower than room temperature.

A further object of the present invention is to provide a process for producing a fine particulate carrier for use in clinical testing having a size of 0.5 to 20 microns and an aldehyde group on the surface by exposing to light or ionizing radiation a system comprising a polymerizable monomer having an aldehyde group and a polymerizable double bond in the same molecule and at least one glass-forming, polymerizable vinyl monomer while maintaining said system at temperatures lower than room temperature.

Still another object of the present invention is to provide a process for producing a fine particulate carrier for use in clinical testing having a size of 0.5 to 20 microns and an aldehyde group on the surface by exposing to light or ionizing radiation an aqueous solution containing a polymerizable monomer having an aldehyde group and a polymerizable double bond in the same molecule and a particle stabilizer while maintaining said system at temperatures lower than room temperature.

A further object of the present invention is to provide a fine particulate carrier for use in clinical testing having a size of 0.5 to 20 microns and an aldehyde group on the surface and which is sensitized with a biologically active material.

A still further object of the present invention is to provide a process for producing a fine particulate carrier for use in clinical testing having a size of 0.5 to 20 microns and an aldehyde group on the surface which is sensitized with a biologically active material by exposing to light or ionizing radiation a system containing a biologically active material plus a polymerizable monomer having an aldehyde group and a polymerizable double bond in the same molecule, or a combination of said polymer with a glass-forming, polymerizable vinyl monomer or a particle stabilizer while maintaining said system at temperatures lower than room temperature.

These and other objects and advantages of the present invention will become apparent by reading the following description.

DETAILED DESCRIPTION OF THE INVENTION

According to the present invention, micro solid particles of a size of 0.5 to 20 microns are produced by polymerizing a polymerizable monomer having an aldehyde group and a polymerizable double bond in the same molecule under exposure to a low dose of light or ionizing radiation while maintaining the monomer at temperatures lower than room temperature, preferably between 5 and −100° C.

One important feature of the present invention is that the intended micro solid particles can be produced by specifying the conditions for radiation-initiated polymerization without incorporating any other material in the above defined polymerizable monomer.

The polymerizable monomer used in the present invention has an aldehyde group and a polymerizable double bond in the molecule, and illustrative examples are croton aldehyde, acrolein, methacrolein and citral. These monomers are vinyl monomers, so if they are subjected to ordinary radiation-initiated polymerization, a block polymerization occurs and a heterogenous and amorphous polymer which certainly is inconsistent with the objects of the present invention is produced. Therefore, we made intensive studies to find the optimum conditions for radiation-initiated polymerization and found that the intended micro solid particles can be obtained by exposing only the monomer to a low dose of light or ionizing radiation under low temperatures so as to ensure a slow progress of polymerization and by then separating the resulting polymer particles from the liquid monomer by filtration.

It is also important for the objects of the present invention that the polymerizable monomer used in the present invention contains an aldehyde group. Since the monomer has an aldehyde group, the surface of the solid fine particles obtained by radiation-initiated polymerization is covered with aldehyde groups. Biologically active materials such as antigens and antibodies can be fixed to these fine particles by simply contacting them with the biologically active material after washing with, for example, water. This introduces a chemical bond strong enough to fix the biologically active material firmly onto the fine particles. The fixing of the biologically active material can be effected simultaneously with the polymerization of the monomer by adding the biologically active material to the polymerization system under exposure to light or ionizing radiation. Since the radiation-initiated polymerization according to the present invention is characterized by low temperatures and low dose levels, there is no possibility that the biologically active material is deactivated after addition to the polymerization system.

The term "biologically active material" as used herein means antigens, enzymes, proteins, microorganism cells, cellular organellas and other components that have certain biological functions. This term is synonymous with biocatalysts or bio-activators.

Any source of ionizing radiation can be used in the present invention, such as electron beams, X-rays and gamma-rays, and the preferred dose of radiation is between $10^4$ and $10^6$ R.

When exposing the polymerizable monomer to light or ionizing radiation, the monomer must be maintained at temperatures lower than room temperature, preferably between 5 and $-100°$ C. For this purpose, any common method may be used. The process of the present invention is not limited to any specific reaction conditions. The monomer may or may not be stirred during the polymerization. The particle size of the polymer can be adjusted to be within the range of 0.5 to 20 microns by properly controlling the polymerization conditions.

As described above, the most important feature of the present invention is to produce micro solid particles by polymerizing the specific monomer under direct exposure to a low dose of light or ionizing radiation in the absence of any additional material such as a reaction medium. However, if desired, the process of the present invention may be carried out in an aqueous phase. The fine particles to be produced by the present invention are highly hydrophobic, so in order to carry out the process of the present invention in an aqueous phase, a stable aqueous dispersion must be prepared with the aid of a protective layer. This protective layer can be formed by adsorbing a surface active material (e.g. ionic or nonionic surfactant) or a water-soluble polymer (polymer protective colloid) onto the surface of the particles. The surface-active material and water-soluble polymer are hereinafter collectively referred to as "particle stabilizers". The present invention includes a system containing not only the polymerizable monomer but also the particle stabilizer. According to this aspect of the present invention, fine particles for use in clinical testing having a size of 0.5 to 20 microns are produced from a polymerization system containing a polymerizable monomer having an aldehyde group and a polymerizable double bond in the same molecule and a particle stabilizer by exposing the system to $10^4$–$10^6$ R of light or ionizing radiation while maintaining the system at temperatures lower than room temperature.

The present invention also includes a process for producing fine particles having a biologically active material fixed thereto upon completion of polymerization. This can be achieved by adding the biologically active material to the polymerization system comprising the polymerizable monomer and the particle stabilizer. According to this aspect of the present invention, an aqueous solution containing the polymerizable monomer having an aldehyde group and a polymerizable double bond in the same molecule is stirred at temperatures lower than room temperature while it is exposed to $10^4$–$10^6$ R of light or ionizing radiation. When the resulting polymer particles have attained a size between 0.5 and 20 microns, a predetermined amount of a biologically active material to be fixed is added to the aqueous solution, which is held at low temperatures, preferably between 0 and 10° C., while it is given another exposure to light or ionizing radiation for a given period until fine particles having the biologically active material fixed to the surface are produced. According to this aspect of the present invention, the aqueous solution undergoes suspension or emulsion polymerization at temperatures low enough to avoid the coagulation of the reaction system, namely in the range of room temperature to 0° C., so the biologically active material can be fixed to the surface of fine polymer particles irrespective of the molecular weight of said material. As a further advantage, the low temperatures used for the polymerization eliminate the possibility of the deactivation of the biologically active material.

The solvent used in the process of the present invention is water. Any conventional method can be used to maintain the reaction system at temperatures low enough to avoid the coagulation of the reaction system, namely in the range of room temperature to 0° C. Examples of the particle stabilizer used in the present invention include water-soluble polymers such as polyvinyl alcohol, methyl cellulose, carboxymethyl cellulose, hydroxyethyl cellulose, casein and polyacrylic acid, and surfactants such as sodium alkylsulfate, sodium alkylsulfonate and alkylammonium hydrochloride. These stabilizers are used in an amount about one tenth of the amount employed in ordinary emulsion polymerization, or a significant amount not more than 0.5% by weight of the reaction system. In ccnsideration of the limited use of the micro particles produced by the present invention, it is important that only a small amount of the particle stabilizer be used.

In the processes described above, only the monomer having an aldehyde group and a polymerizable double bond in the same molecule is used as the polymerizable monomer. But as a result of further studies, we have found that fine particles having various properties can be produced by copolymerizing said polymerizable monomer with another type of polymerizable monomer. Therefore, the present invention also includes a system containing not only the above described polymerizable monomer but also a glass-forming, polymerizable vinyl monomer.

The term "glass-forming polymerizable vinyl monomer" as used herein means a polymerizable monomer that can be supercooled at low temperatures without crystallization and without losing its polymerizability. Polymerization of this type of monomer in the supercooled state may be regarded as solid-phase polymerization in the amorphous state, and because of its great ability to polymerize at low temperatures, said monomer is a very effective material for use in cold polymerization adapted to the fixing of a biologically avtive material. Most biologically active materials are thermally unstable, and in order to avoid their deactivation, they are preferably fixed at the lowest possible temperature. One effective means for achieving polymerization at low temperatures is radiation-initiated polymerization, and in consideration of the high polymerizability of the glass-forming vinyl monomer under irradiation at low temperatures, using this type of polymerizable monomer can be regarded as another important feature of the present invention.

The glass-forming, polymerizable vinyl monomer contains in its molecule a hydrogen-bonding functional group of a suitable strength, a bulky or highly assymmetric substituent, or a bond such as an ether bond having small free energy of rotation. One or more monomers may be selected from among the glass-forming vinyl compounds having the following formulas:

$$CH_2=CX-\underset{\underset{O}{\|}}{C}-O(CH_2)_nOR_1 \qquad (a)$$

wherein X is H or methyl and $R_1$ is H or

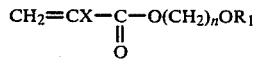

(wherein X is H or methyl; and n is an integer of 4 to 10);

$$CH_2=CX-\underset{\underset{O}{\|}}{C}-O-(R_2)_m-\underset{\underset{O}{\|}}{C}-CX=CH_2 \qquad (b)$$

wherein X is H or methyl; $R_2$ is —$CH_2CH_2O$—,

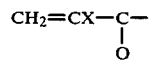

and n is an integer of 1 to 3;

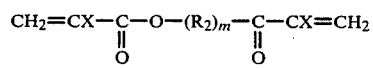

wherein X is H or methyl;

$$CH_2=CX-\underset{\underset{O}{\|}}{C}-O-R_3-O-R_4 \qquad (d)$$

wherein X is H or methyl; $R_3$ is a straight- or branched-chain alkylene group having 1 to 10 carbon atoms; and $R_4$ is a vinyl or an alkyl group having 1 to 10 carbon atoms;

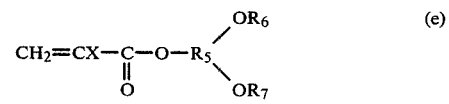

wherein $R_5$ is alkane($C_1$-$C_5$)-yl-ylide, alkylene($C_1$-$C_5$) amino group; $R_6$ and $R_7$ are each H, an alkyl group having 1 to 5 carbon atoms, an alkylamino group having 1 to 5 carbon atoms, a hydroxyalkyl group having 1 to 5 carbon atoms, an allyl or vinyl group;

$$CH_2=CX-\underset{\underset{O}{\|}}{C}-R_3-O-R_8-O-R_4 \qquad (f)$$

wherein X, $R_3$ and $R_4$ are the same as defined above; $R_8$ is the same as $R_3$; $R_3$ and $R_8$ may be the same or different;

$$CH_2=CX-\underset{\underset{O}{\|}}{C}-O-R_3-\underset{\underset{O}{\|}}{C}-R_4 \qquad (g)$$

wherein X, $R_3$ and $R_4$ are the same as defined above;

$$CH_2=CX-\underset{\underset{O}{\|}}{C}-O-R_3-\underset{\underset{O}{\|}}{C}-O-R_4 \qquad (h)$$

wherein X, $R_3$ and $R_4$ are the same as defined above;

$$CH_2=CX-\underset{\underset{O}{\|}}{C}-O-R_{11} \qquad (i)$$

wherein X is the same as defined above; $R_{11}$ is benzyl, toluyl, xylyl, phenyl, furfuryl, naphthyl, phthalyl, cyclohexyl, cyclophenyl, cycloheptyl, cyclobutyl, pyridyl or 2-oxopyrrolidinyl group;

$$R_9-\underset{\underset{O}{\|}}{C}-(CH_2-O-\underset{\underset{O}{\|}}{C}-CX=CH_2)_3 \qquad (j)$$

wherein X is the same as defined above; $R_9$ is an ethyl or propyl group; and $$CH_2=CX-\underset{\underset{O}{\|}}{C}-O-O-R_{10}-O-\underset{\underset{O}{\|}}{C}-CX=CH_2 \qquad (k)$$

wherein X is the same as define above; $R_{10}$ is isopropylene, isobutylene, a branched-chain alkylene group having 1 to 5 carbon atoms,

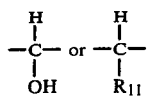

(wherein $R_{11}$ is the same as defined above).

Specific examples of the glass-forming, polymerizable vinyl monomers that can be used in the present invention include: hydroxyethyl methacrylate, hydroxyethyl acrylate, hydroxypropyl acrylate, hydroxypropyl methacrylate, diethylene glycol methacrylate, diethylene glycol acrylate, triethylene glycol methacrylate, triethylene glycol acrylate, tetraethylene glycol acrylate, tetraethylene glycol methacrylate, polyethylene glycol methacrylate, polyethylene glycol acrylate, diethylene glycol dimethacrylate, diethylene glycol diacrylate, methoxydiethylene glycol dimethacrylate, methoxydiethylene glycol diacrylate, methoxytetraethylene glycol dimethacrylate, neopentyl glycol dimethacrylate, hexanediol monomethacrylate, glycidyl methacrylate, glycidyl acrylate, heptanediol monomethacrylate, butanediol monomethacrylate, ethylene glycol diacrylate and propylene glycol dimethacrylate.

According to the present invention, fine particles having various properties can be produced by copolymerizing the polymerizable monomer having an aldehyde group and a polymerizable double bond in the same molecule with the glass-forming, polymerizable vinyl monomer. By using a hydrophobic, glass-forming vinyl monomer, particles having high strength can be produced. By using a hydrophilic vinyl monomer such as hydroxyethyl methacrylate or acrylic acid, a given nunmber of particles can be produced within a short period of time and the number of the aldehyde groups present on the surface of the particles can be freely controlled.

In a specific embodiment, the two monomers may be dissolved in water or an organic solvent and the resulting solution may be subjected to radiation-initiated polymerization. In case of polymerization in the aqueous solution, a water-soluble polymer such as polyvinyl alcohol or a surfactant such as sodium dodecylsulfate may be used as the particle stabilizer. In practicing the process of the present invention, the reaction temperature is not more than room temperature, preferably in the range of 5° to −100° C. The dose of radiation is in the range of $10^4$ to $10^6$ R. If the polymerization reaction is effected at temperatures higher than 0° C., the reaction system needs to be agitated, but at sub-zero temperatures, the reaction system containing the polymerizable monomers is preferably frozen before it is subjected to radiation-initiated polymerization. This technique has the advantage of simplified procedures. The reaction system may be even cooled to a solid form before it is subjected to radiation-initiated polymerization. This method is also capable of forming particles having a uniform size of 1 to 2 microns, which is the advantage that is obtainable only when the two monomers are copolymerized.

The fine particles produced by either of the methods described above are covered with aldehyde groups. Therefore, a biologically active material such as an antigen or antibody can be readily fixed to these particles by simply washing them with, for example, water and then contacting the particles with the biologically active material under specific conditions. This introduces a chemical bond that permits the biologically active material to be firmly fixed onto the surface of the fine particles. Biologically active materials cannot be firmly fixed to the conventional latex particles and are often dislodged because the bonding mechanism depends on the non-specific adsorption onto the latex particles. Therefore, when the fine particles according to the present invention are used as carriers in immunochemical assaying of substances that are present in body fluids in trace amounts, the detection accuracy achieved is higher than that obtained by using conventionally prepared fine particles.

The micro solid particles according to the present invention can be used as carriers not only in clinical testing depending on general immunological reactions but also in clinical determinations using various binding reactions such as receptor reaction and lectin reaction. Furthermore, the particles can be employed in separating and purifying biologically active materials with the aid of these immunological and binding reactions The advantages of the present invention are hereunder described in greater detail by reference to the following examples which are given here for illustrative purposes only and are by no means intended to limit the scope of the invention. In the examples that follow, all percentages and parts are by weight.

EXAMPLE 1

A glass container accomodating 10 g of acrolein was put into a cooling medium (−24° C.) made of carbon tetrachloride and liquid nitrogen until the container was adequately cooled. While maintaining the container at −24° C., the acrolein was polymerized by irradiation with gamma-rays from $Co^{60}$ for 1 hour at a dose rate of $5 \times 10^5$ R/hr. After completion of the polymerization, the resulting particles were separated by a centrifuge, washed with methanol three times to remove the unreacted acrolein, washed with water twice, and subsequently dried. The particles of the final product weighed 1.59 g and had a size between 2 and 3 microns.

EXAMPLE 2

Rabbits were immunized with human IgG to produce anti-human IgG containing rabbit sera. Gamma-globulin fractions were obtained from the sera and dissolved in a 0.1 M $NaHCO_3$ buffer (pH: 8.94) containing 0.5 M NaCl. The particles prepared in Example 1 were sensitized with the antibody in the following manner. The particles (10 mg) were dissolved in the buffer (3 ml) and the resulting solution was left at room temperature for 2 hours. The solution was mixed with a 0.2 M aqueous glycine solution, and the mixture was left at room temperature for 2 hours. By centrifuging the mixture at 3,000 rpm for 10 minutes, glycine-coated particles sensitized with anti-human IgG rabbit IgG. These particles were suspended in a 0.01 M PBS buffer. A suspension containing $2.3 \times 10^8$ particles per milliliter was mixed with human IgG (0.67 mg/ml), and the mixture was left to stand at 37° C. for 1 hour. Aggregation of the particles was distinct.

EXAMPLE 3

Croton aldehyde (10 g) in a glass container was cooled to 0° C. with ice. While maintaining the container at 0° C., the croton aldehyde was polymerized by irradiation with gamma-rays from $Cs^{137}$ for 2 hours at a dose rate of $4 \times 10^5$ R/hr. After completion of the polymerization, the resulting particles were recovered by centrifugation (3,000 rpm×10 min) and washed with methanol and water as in Example 1. The fine particles as the final product weighed 1 g and had a size between 1 and 2 microns.

EXAMPLE 4

Rabbits were immunized with human chorionic gonadotropin (HCG) and gamma-globulin fractions were obtained from the resulting anit-HCG containing rabbit sera. A glycine buffer containing 0.1% of the gamma-globulin fractions was prepared and mixed with 20 mg of the fine particles prepared in Example 3. After being left at room temperature for 30 minutes, the mixture was centrifuged (3,000 rpm×10 min) to produce glycine-coated particles sensitized with anti-HCG rabbit IgG. These particles were suspended in a glycine buffer and used as an HCG detection reagent. These anti-HCG/IgG sensitized particles agglomerated in the presence of 0.2 IU/ml of HCG.

EXAMPLE 5

Acrolein (5 g) in a glass container was cooled to −11° C. with a cooling medium made of ice and KCl. While maintaining the container at −11° C., the acrolein was polymerized by irradiation with gamma-rays from $Co^{60}$ for 3 hours at a dose rate of $1\times 10^5$ R/hr. The resulting polymer particles had a size of 3 to 4 microns.

EXAMPLE 6

The fine particles prepared in Example 5 were checked for their effectiveness as a marker for human lymphocytes (B cells) in the following manner.

Rabbits were immunized with human IgG, and gamma-globulin fractions were obtained from the resulting human IgG-containing rabbit sera. The fractions were dissolved in a 0.1 M $NaHCO_3$ buffer (pH: 8.94) containing 0.5 M NaCl to prepare a sensitizing solution. The particles (10 mg) prepared in Example 5 were put into the sensitizing solution and the mixture was left at room temperature for 30 minutes. To the mixture, 0.2 M glycine solution was added, and the resulting mixture was left to stand at room temperature for an additional 30 minutes. By centrifuging at 3,000 rpm for 5 minutes, glycine-coated particles sensitized with anti-human IgG rabbit IgG were obtained. These particles were suspended in a 0.01 M PBS buffer.

The sensitized particles (5 mg) were added to two samples of Hank's solution (with 0.2% BSA), one containing Fujimaki cells (B cell line) and the other containing Molt cells (T cell line). Both cells were cultured leucocyte cells. The solutions were left at 37° C. for 1 hour. No particle aggregation occurred in the solution containing the Molt cells, but in the solution containing Fujimaki cells, many particles aggregated around the cells.

EXAMPLE 7

Acrolein (5 g) was put in a glass container and sensitized with 1 ml of a solution prepared by dissolving 10 mg of anti-human IgG rabbit IgG fractions in 10 ml of 0.1 M $NaHCO_3$ buffer. The IgG fractions were obtained by immunizing rabbits with human IgG. While maintaining the container at 0° C., the solution was irradiated under stirring with gamma-rays from $Co^{60}$ for 2 hours at a dose rate of $1\times 10^5$ R/hr. By this procedure, polyacrolein particles (2-3 microns) sensitized with anti-human IgG rabbit IgG were produced.

EXAMPLE 8

The sensitized particles prepared in Example 7 were washed with 0.01 M PBS buffer five times, and subsequently suspended in 0.01 M PBS buffer. A suspension containing $5\times 10^8$ particles per milliliter was mixed with 0.5 mg/ml of human IgG, and the mixture was left at 37° C. for 30 minutes. A distinct aggregation of the particles was observed.

EXAMPLE 9

Acrolein (10 parts), water (85 parts) and sodium dodecylsulfate (1 part) were put into a container and mixed thoroughly to make a uniform mixture. The two monomers were copolymerized by irradiation with gamma-rays from $Co^{60}$ for 2 hours at a dose rate of $5\times 10^5$ R/hr while maintaining the container at room temperature.

Rabbits were immunized with human IgG to produce anti-human IgG containing rabbit sera. Gamma-globulin fractions (5 mg) obtained from these sera were dissolved in 0.1 M $NaHCO_3$ buffer (pH: 8.94). One part of the resulting solution was put into the container. While maintaining the container at 4° C., the contents were irradiated with gamma-rays from $Co^{60}$ for 1 hour at a dose rate of $5\times 10^5$ R/hr. Thereafter, the resulting fine particles (1-2 microns) were recovered and washed with 0.01 M PBS buffer and suspended in the same buffer. A suspension containing $2\times 10^8$ particles per milliliter was mixed with human IgG (0.60 mg/ml) and the mixture was left at 37° C. for 1 hour. The aggregation of the particles was distinct.

EXAMPLE 10

Acrolein (5 parts), water (90 parts) and polyvinyl alcohol (3 parts) were put into a container and mixed thoroughly to make a uniform mixture. The two monomers were copolymerized by irradiation under stirring with UV radiation from a mercury lamp for 5 hours while the container was maintained at room temperature.

Rabbits were immunized with human chorionic gonadotropin (HCG) to produce anti HCG containing rabbit sera. Gamma-globulin fractions obtained from these sera were dissolved in a glycine buffer, and the solution was given another UV irradiation for 1 hour. Particles of a size of 0.5 to 2 microns were obtained. These particles (10 mg) were put into a 0.2 M aqueous glycine solution and stirred. The resulting fine particles sensitized with anti HCG IgG rabbit IgG were suspended in a glycine buffer to make an HCG detection reagent. The fine particles formed an aggregate in the presence of 0.15 IU/ml of HCG.

EXAMPLE 11

One part of a monomer mixture (acrolein: 0.7 part, and hydroxyethyl methacrylate: 0.3 part) was intimately blended with 9 parts of a 1% aqueous solution of polyvinyl alcohol, and the resulting mixture was cooled at −78° C. while it was irradiated with gamma-rays from $Co^{60}$ for 1 hour at a dose rate of $1\times 10^6$ R/hr. The resulting fine particles had a maximum size of 1.4 microns.

EXAMPLE 12

The fine particles prepared in Example 11 were washed with 1% PBS buffer three times and subsequently dried. Rabbits were immunized with human chorionic gonadotropin (HCG) to produce anti HCG containing rabbit sera. Gamma-globulin fractions were dissolved in a glycine suspension at a concentration of 0.1%. The dried particles (10 mg) of acrolein-hydroxyethyl methacrylate copolymer were dissolved in the glycine solution, which was left to stand at room temperature for 30 minutes. The sensitized particles were separated by sentrifugation and suspended in a glycine solution to form an HCG detection reagent. The particles aggregated distinctly in the presence of 0.1 IU/ml of HCG.

EXAMPLE 13

Three parts of a monomer mixture (1.5 parts of citral and 1.5 parts of triethylene glycol diacrylate was put into a container and intimately blended with 7 parts of a 1% aqueous solution of polyvinyl alcohol. The resulting mixture was irradiated under agitation at 4° C. with gamma-rays from $Co^{60}$ for 2 hours at a dose rate of $1 \times 10^6$ R/hr. One milliliter of a solution having 5 mg of anti-human IgG rabbit IgG dissolved in 0.1 M NaHCO$_3$ buffer (pH: 8.94) was put into the container, and the contents were irradiated with gamma-rays for 30 minutes under the same conditions as described above. The resulting sensitized particles had a size of 2-3 microns. They were washed with 0.01 M PBS buffer and suspended in the same buffer. A suspension containing $2 \times 10^8$ particles/ml was mixed with 0.5 mg/ml of human IgG, and the mixture was left to stand at 37° C. for 1 hour. A distinct aggregation of the particles occurred.

What is claimed is:

1. A process for producing a fine particulate carrier for use in clinical testing having a generally uniform size within the range of 0.5 to 20 microns and an aldehyde group on the surface by exposing to light or ionizing radiation, at temperatures in the range of between 5° and −100° C., a polymerizable monomer having an aldehyde group and a polymerizable double bond in the same molecule while maintaining said monomer at temperatures within said temperature range.

2. A process for producing a fine particulate carrier for use in clinical testing having a generally uniform size within the range of 0.5° to 20 microns and an aldehyde group on the surface by exposing to light or ionizing radiation, at temperatures between 5° and −100° C., a system comprising a polymerizable monomer having an aldehyde group and a polymerizable double bond in the same molecule and at least one glass-forming, polymerizable vinyl monomer, while maintaining said system at temperatures within said temperature range.

3. A process for producing a fine particulate carrier for use in clinical testing having a generally uniform size within the range of 0.5 to 20 microns and an aldehyde group on the surface by exposing to light or ionizing radiation, at temperatures between 5° and −100° C., an aqueous solution containing a polymerizable monomer having an aldehyde group and a polymerizable double bond in the same molecule and a particle stabilizer selected from the group consisting of water-soluble polymers and surfactants, while maintaining said system at temperatures within said temperature range.

4. A process for producing a fine particulate carrier for use in clinical testing having a generally uniform size within the range of 0.5 to 20 microns and an aldehyde group on the surface which is sensitized with a biologically active material by exposing to light or ionizing radiation, at temperatures between 5° and −100° C., a system containing a biologically active material plus a polymerizable monomer having an aldehyde group and a polymerizable double bond in the same molecule, or a combination of said polymer with a glass-forming, polymerizable vinyl monomer or a particle stabilizer selected from the group consisting of water-soluble polymers and surfactants, while maintaining said system at temperatures within said temperature range.

5. A process according to claim 1 wherein the dosage of radiation applied is $10^4$–$10^6$R.

6. A process according to claim 2 wherein the dosage of radiation applied is $10^4$–$10^6$R.

7. A process according to claim 3 wherein the dosage of radiation applied is $10^4$–$10^6$R, and wherein said particle stabilizer is present in an amount not more than about 0.5% by weight of the reaction system.

8. A process according to claim 4 wherein the dosage of radiation applied is $10^4$–$10^6$R, and wherein said particle stabilizer is present in an amount not more than about 0.5% by weight of the reaction system.

9. A procs according to claim 1 wherein said polymerizable monomer having an aldehyde group and a polymerizable double bond is selected from the group consisting of croton aldehyde, methacrolein and citral.

10. A process according to claim 2 wherein said polymerizable monomer having an aldehyde group and a polymerizable double bond is selected from the group consisting of croton aldehyde, methacrolein and citral.

11. A process according to claim 3 wherein said polymerizable monomer having an aldehyde group and a polymerizable double bond is selected from the group consisting of croton aldehyde, methacrolein and citral.

12. A process according to claim 4 wherein said polymerizable monomer having an aldehyde group and a polymerizable double bond is selected from the group consisting of croton aldehyde, methacrolein and citral.

13. A process according to claim 1 further comprising adding a biologically active material to said fine particulate carrier while maintaining a temperature no greater than about 10° C. and exposing to light or ionizing radiation to fix the biologically active material to the fine particulate carrier.

14. A process according to claim 2 further comprising adding a biologically active material to said fine particulate carrier while maintaining a temperature no greater than about 10° C. and exposing to light or ionizing radiation to fix the biologically active material to the fine particulate carrier.

15. A process according to claim 3 further comprising adding a biologically active material to said fine particulate carrier while maintaining a temperature no greater than about 10° C. and exposing to light or ionizing radiation to fix the biologically active material to the fine particulate carrier.

* * * * *

UNITED STATES PATENT AND TRADEMARK OFFICE
CERTIFICATE OF CORRECTION

PATENT NO. : 4,552,633
DATED : November 12, 1985
INVENTOR(S) : KUMAKURA et al

It is certified that error appears in the above-identified patent and that said Letters Patent is hereby corrected as shown below:

[73] Assignees: The full name of the second assignee is:

Japan Immunoresearch Laboratories Co., Ltd.

Signed and Sealed this

Third Day of June 1986

[SEAL]

Attest:

DONALD J. QUIGG

Attesting Officer   Commissioner of Patents and Trademarks